US010639300B2

(12) United States Patent
Solis Herrera

(10) Patent No.: US 10,639,300 B2
(45) Date of Patent: May 5, 2020

(54) COMPOSITIONS AND METHODS FOR TREATING NASAL AND PARANASAL MUCOSA DISEASES WITH NICOTINIC ACETYLCHOLINE RECEPTOR AGONISTS

(71) Applicant: Arturo Solis Herrera, Aguascalientes (MX)

(72) Inventor: Arturo Solis Herrera, Aguascalientes (MX)

(*) Notice: Subject to any disclaimer, the term of this patent is extended or adjusted under 35 U.S.C. 154(b) by 0 days.

(21) Appl. No.: 16/090,317

(22) PCT Filed: Apr. 12, 2017

(86) PCT No.: PCT/IB2017/000764
§ 371 (c)(1),
(2) Date: Oct. 1, 2018

(87) PCT Pub. No.: WO2017/178897
PCT Pub. Date: Oct. 19, 2017

(65) Prior Publication Data
US 2019/0111038 A1 Apr. 18, 2019

(30) Foreign Application Priority Data

Apr. 12, 2016 (AU) ................. 2016901359

(51) Int. Cl.
| A61K 31/44 | (2006.01) |
| A61K 31/60 | (2006.01) |
| A61K 31/4439 | (2006.01) |
| A61K 9/00 | (2006.01) |
| A61K 9/08 | (2006.01) |
| A61K 47/38 | (2006.01) |
| A61P 11/02 | (2006.01) |
| A61K 9/12 | (2006.01) |
| A61K 47/12 | (2006.01) |
| A61N 5/06 | (2006.01) |

(52) U.S. Cl.
CPC ........ *A61K 31/4439* (2013.01); *A61K 9/0043* (2013.01); *A61K 9/08* (2013.01); *A61K 9/12* (2013.01); *A61K 47/38* (2013.01); *A61P 11/02* (2018.01); *A61K 47/12* (2013.01); *A61N 5/0603* (2013.01); *A61N 2005/0607* (2013.01)

(58) Field of Classification Search
CPC ................................ A61K 31/44; A61K 31/60
USPC .................................................. 514/357, 161
See application file for complete search history.

(56) References Cited

U.S. PATENT DOCUMENTS

| 4,579,858 A | 4/1986 | Ferno et al. |
| 6,277,855 B1 | 8/2001 | Yerxa |
| 6,596,740 B2 | 7/2003 | Jones |
| 2006/0003989 A1 | 1/2006 | Quay et al. |
| 2009/0197921 A1 | 8/2009 | Solis Herrera |
| 2012/0270907 A1 | 10/2012 | Herrera |
| 2014/0207214 A1 | 7/2014 | Oberreiter et al. |

FOREIGN PATENT DOCUMENTS

| CN | 104706556 A | 6/2015 |
| NZ | 572366 A | 2/2012 |
| RU | 2290224 C2 | 12/2006 |
| WO | 9427576 A1 | 12/1994 |
| WO | 9600071 A1 | 1/1996 |
| WO | 2003013653 A1 | 2/2003 |
| WO | 2004052365 A1 | 6/2004 |
| WO | 2005023227 A2 | 3/2005 |
| WO | 2006005195 A1 | 1/2006 |
| WO | 2007129879 A1 | 11/2007 |
| WO | 2008062453 A2 | 5/2008 |
| WO | 2009069126 A1 | 6/2009 |
| WO | 2015084544 A1 | 6/2015 |

OTHER PUBLICATIONS

Int'l Search Report and Written Opinion dated Oct. 5, 2017 in Int'l Application No. PCT/IB17/00764.
Marques-Marinho et al. "Cellulose and Its Derivatives Use in the Pharmaceutical Compounding Practice," Chapter 8, Cellulose—Medical, Pharmaceutical and Electronic Applications. pp. 141-162. (2013).
Aliev et al., "Human Photosynthesis, the ultimate answer to the long term mystery of Kleiber's law or E=M3/4: Implication in the context of gerontology and neurodegenerative diseases", Open Journal of Psychiatry, 3, pp. 408-421, 2013.
Examination Report dated Mar. 14, 2019 in AU Application No. 2017250514.
Han et al., "Nicotine, an anti-inflammation molecule", Inflammation & Cell Signaling, 1, E155, 8 pages, 2014.
First Examination Report dated May 14, 2019 in NZ Application No. 744942.
Cruz et al., "Rhinosinusitis and Aspirin-Exacerbated Respiratory Disease", Journal of Allergy, vol. 2012, 8 pages, 2012.
Domino, E.F., "Pharmacological Significance of Nicotine. Analytical Determination of Nicotine and Related compounds and their Metabolites", Elsevier Science B.V., pp. 1-11, (1999).
Gantson, et al., "Lipids, carbohydrate, macromolecules, biosynthesis", General Organic Chemistry M. Chemistry, vol. 11, p. 2 , 547-549 (1986).
Mashkovsky, M.D., "Medicaments", Novaya Volna, vol. 1, p. 188-189, (2001).
Office Action Issued in Russian Patent App. No. 2018139338 dated Jul. 4, 2019. (with English translation).

(Continued)

*Primary Examiner* — Raymond J Henley, III
(74) *Attorney, Agent, or Firm* — Panitch Schwarze Belisario & Nadel LLP

(57) ABSTRACT

Methods of treating and preventing conditions of a nasal or paranasal mucous membrane are described. The methods include administering a pharmaceutical composition including a nicotinic acetylcholine receptor (nAChR) agonist, such as (S)-(1-methyl-2-pyrrolidinyl)-pyridine, or a pharmaceutically acceptable salt, analog, precursor or derivative thereof. The methods can be used to treat a wide variety of conditions of the nasal or paranasal mucous membrane, such as nasal congestion and nose bleeds.

20 Claims, No Drawings

(56) References Cited

OTHER PUBLICATIONS

Search Report issued in Russian Patent App. No. 2018139338 dated Jul. 1, 2019.
Office Action dated Aug. 19, 2019 in Japanese Patent Application No. 2018-553136. (with English translation).
Office Action dated Aug. 22, 2019 in Canadian Patent Application No. 3,014,725.
Extended European Search Report dated Nov. 21, 2019 in EP Application No. 17782003.2.
Gothe et al., "Nicotine: A Differenct Approach to Treatment of Obstructive Sleep Apnea," CHEST, vol. 87, No. 1, pp. 11-17 (1985).
Hurt et al., "Nicotine Nasal Spray for Smoking Cessation: Pattern of Use, Side Effects, Relief of Withdrawal Symptoms, and Cotinine Levels," Mayo Clinic Proceedings, vol. 73, No. 2, pp. 118-125 (1998).
Comer et al., "Inflammatory and cytotoxic effects of acrolein, nicotine, acetylaldehyde and cigarette smoke extract on human nasal epithelial cells," BMC Pulmonary Medicine, vol. 14, No. 32, pp. 1-11 (2014).
Mishra et al., "Nicotine Inhibits Fce RI-Induced Cysteinyl Leukotrienes and Cytokine Production without Affecting Mast Cell Degranulation Through a7/a9/a10-Nicotinic Receptors," The Journal of Immunology, pp. 588-596 (2014).
Office Action dated Jan. 14, 2020 in JP Application No. 2018553136.
Yamamoto et al., "Anti-Allergic Role of Cholinergic Neuronal Pathway in a7 Nicotinic ACh receptors on Mucosal Mast Cells in a Murine Food Allergy Model,"PLOS One, vol. 9, No. 1, pp. 1-11 (2014).

COMPOSITIONS AND METHODS FOR TREATING NASAL AND PARANASAL MUCOSA DISEASES WITH NICOTINIC ACETYLCHOLINE RECEPTOR AGONISTS

CROSS-REFERENCE TO RELATED APPLICATIONS

This application is a Section 371 of International Application No. PCT/IB2017/000764, filed Apr. 12, 2017, which was published in the English language on Oct. 19, 2017 under International Publication No. WO 2017/178897 A2, which claims priority under 35 U.S.C. § 119(d) to Australian Provisional Patent Application No. 2016901359, filed Apr. 12, 2016, the disclosures of which are herein incorporated by reference.

FIELD OF THE INVENTION

The invention relates to methods and compositions for treating and preventing conditions of the nasal and paranasal mucous membranes.

BACKGROUND

The nose is a complex organ with connections to the respiratory tract and the central nervous system. The nose has a nose cavity open to the face at the anterior nares (nostrils) and extending posteriorly to the pharynx. The interior surface area of the nose is increased by the presence of multiple nasal turbinates, which are structures on the side walls of the inside of the nose having a cross-section that represents fine tear shapes hanging within the nasal cavity. The nasal turbinates include a superior turbinate, a middle turbinate and an inferior turbinate. Also included in the nasal cavity are olfactory bulbs and olfactory nerves for the sense of smell. The nasal cavity is also connected to and continuous with the paranasal sinuses or passages. The paranasal sinuses are located generally behind the forehead and cheekbones. The principal nasal sinuses are a frontal sinus, a sphenoidal sinus, a maxillary sinus and an ethmoid sinus. The nasal cavity and the paranasal sinuses are lined generally throughout with a ciliated mucous membrane. The orifice of the auditory or Eustachian canal to the ear is located at the posterior of the nasal cavity.

Part of the function of the nose is to provide pre-warming and humidification of inhaled air as well as some heat recovery and moisture recovery of air exhaled from the lungs. In addition, particulate filtering and smelling of the air is also performed by the nose with the sense of smell also contributing to the sense of taste. The nose also contributes to the speech faculty. The mucous secreting membrane together with the cilia performs a filtering function and a mucosal-ciliary transport system for the filtered material. The amount of mucous being secreted in 24 hours can be up to 1 liter. Mucous membranes of the nasal cavity and paranasal sinuses can more than double their secretion when inflamed or stimulated. The mucous is also one of the first lines of immune defense due to the presence of immunoglobulins within the mucous. The blood supply, local membrane responses, autonomic nerves and the central nervous system contribute to the level of control of mucous secretion and swelling of the nasal membranes. Furthermore, the membranes of the nose and paranasal sinuses are highly vascular, such that compounds absorbed by the membranes can be readily transported to the blood vessels of the nose and paranasal sinuses and subsequently to the rest of the body by the circulatory system.

Nasal congestion can be defined as the blockage of the nasal passages and paranasal sinuses usually from the swelling of membranes lining the nose due to vasodilatation of local blood vessels and/or inflammation of the membranes. Nasal congestion can also be referred to as nasal blockage, nasal obstruction, blocked nose, stuffy nose or stuffed up nose. Nasal congestion can have many multi-factorial causes and can range from a mild annoyance to a life-threatening condition.

For example, nasal congestion can interfere with hearing and consequently delay speech development in young children. In children and adults, nasal congestion can interfere with sleep, contribute to snoring, and is sometimes associated with sleep apnea. In general nasal congestion, can also cause, or is associated with postnasal drainage, facial pressure and pain, headaches, chronic or recurrent sinusitis and sinus infections. Other associated effects of nasal congestion in a general order of frequency include: dripping of mucous membrane secretions down the throat, abnormal taste sensations, feelings of dryness in the upper respiratory tract, drowsiness, nasal irritation, loss of the sense of smell, and burning sensations within the nose and nose bleeds. Co-morbidity conditions are often overlooked, but can contribute significantly to the burden of nasal congestion and allergic rhinitis (AR) for a patient. Examples of co-morbidity conditions reported in a significant number of patients include asthma, nasal polyps (nasal polyposis) and sleep apnea. Nasal congestion in an infant in the first few months of life can interfere with breast feeding and in severe cases can cause life threatening respiratory distress.

The symptoms of nasal congestion, such as ear or hearing issues, loss of smell, facial pain, post nasal drip, headache, itchy nose, itchy eyes, watering eyes, runny nose, sneezing, and stuffed nose are commonly reported by patients to be extremely or moderately bothersome. For surveyed sufferers in the case of edema of the mucous membranes, the symptoms are reported as "well controlled" in 29% of cases, "somewhat controlled" in 41% of cases, and "poorly controlled" in 21% of cases. See, e.g., Manning S C. "*Medical management of nasosinus infectious and inflammatory disease.*" In: Flint P W, Haughey B H, Lund L J, et al, eds. *Cummings Otolaryngology: Head & Neck Surgery.* 5th ed. Philadelphia, Pa.: Mosby Elsevier; 2010: chap 50, the contents of which are incorporated herein by reference.

Most patients with nasal congestion report that nasal symptoms have a significant adverse impact on their daily life, a problem not always appreciated by physicians and society in general. Patients have reported that the degree of affliction of associated nasal symptoms, such as reduced productivity, poor concentration, thirst, headache, and tiredness, varies from somewhat troublesome to very troublesome. Other consistent findings among nasal congestion sufferers are high rates of sleep disorders, daytime fatigue, and memory impairment and reduced work productivity.

The changes in the histopathology of the mucous membranes that have been reported for nasal congestion include greater goblet cell hyperplasia, thicker epithelium, changes in the basal membrane and the presence of a diverse range of cells associated with inflammation. There have been several descriptions of the histopathology of nasal membrane inflammation, including metaplasia, pseudo thickening of the basal membrane and infiltration of the mucous membrane by inflammatory cells, such as eosinophils, neutrophils, CD8 T-lymphocytes and macrophages. The cellular and molecular mechanisms of the inflammatory process in the upper airways of patients with nasal congestion have been studied increasingly over the last few decades. However, to the best of the knowledge of the inventor, no studies to date have been conclusive as to treatment protocols.

Nasal congestion is a cardinal symptom of allergic rhinitis (AR), an inflammatory response of the nasal and paranasal mucous membranes. The inflammatory response of the mucous membranes can be attributed to IgE antibodies. The prevalence of AR is increasing worldwide, a trend that has been attributed to a variety of factors, such as changing global climate conditions, improvements in hygiene, changes in diet, and increased obesity. AR, whether atopic or non-atopic, is a risk factor for the development of asthma. Nasal congestion and runny nose were identified as the most irritable symptoms of AR and were the most frequently reported symptom of AR. Accordingly, the alleviation of nasal congestion and runny nose is often a primary goal of AR therapy and management.

It is estimated that prescription only medications for the current management of allergic rhinitis symptoms are used by 12 to 24% of sufferers, whereas over-the-counter (OTC) medicines are estimated to be used by up to 50% of other sufferers of AR. Orban N T, Saleh H, Durham S R. "*Allergic and non-allergic rhinitis*". In: Adkinson N F Jr, ed. Middleton's Allergy: Principles and Practice. 7th ed. Philadelphia, Pa.: Mosby Elsevier; 2008: Chap 55, the contents of which are incorporated herein by reference.

Classes of drugs that can be used to treat AR include antihistamines, corticosteroids, mast cell stabilizers, decongestants, nasal anti-cholinergics, and leukotriene receptor antagonists. Intranasal corticosteroids typically provide significantly greater relief of nasal congestion than oral antihistamines. However, the adverse side-effects of corticoids may preclude their widespread use.

None of these prior art methods, drugs, treatments and/or therapies provides an entirely satisfactory solution to the alleviation or treatment of the symptoms or underlying causes of nasal congestion, nasal allergies, allergic rhinitis and other disease conditions of the nasal and paranasal mucous membranes.

BRIEF SUMMARY OF THE INVENTION

The present invention aims to provide a novel therapeutic approach to treating and/or preventing conditions of the nasal and paranasal mucous membranes that overcomes or ameliorates the disadvantages of the prior art.

In one general aspect, the invention relates to a method of treating or preventing a condition of a nasal or paranasal mucous membrane or symptom thereof in a subject with a nicotinic acetylcholine receptor (nAChR) agonist.

In one embodiment, a method of treating or preventing a condition of a nasal or paranasal mucous membrane, or symptom thereof in a subject comprises administering to the nasal or paranasal mucous membrane of the subject a therapeutically effective amount of a pharmaceutical composition comprising a nicotinic acetylcholine receptor (nAChR) agonist and at least one pharmaceutically acceptable diluent, excipient, or carrier.

In a preferred embodiment, the nAChR agonist is (S)-(1-methyl-2-pyrrolidinyl)-pyridine or a pharmaceutically acceptable salt, analog, precursor, or derivative thereof.

In a preferred embodiment, the pharmaceutically acceptable diluent, excipient, or carrier comprises methylcellulose, preferably at a concentration of about 0.5% by weight to 1% by weight based on a total weight of the composition.

In a particular embodiment, a method of treating a condition of a nasal or paranasal mucous membrane, or symptom thereof in a human subject in need of the treatment comprises nasally administering to the nasal or paranasal mucous membrane of the subject a therapeutically effective amount of an aqueous pharmaceutical composition comprising about 0.1 mg/ml to 2.0 mg/ml of (S)-(1-methyl-2-pyrrolidinyl)-pyridine or a pharmaceutically acceptable salt thereof and at least one pharmaceutically acceptable diluent, excipient, or carrier, wherein the condition is selected from the group consisting of nasal congestion and nasal hemorrhages ("nose bleeds").

In another general aspect, the invention relates to a pharmaceutical composition comprising:
a. (S)-(1-methyl-2-pyrrolidinyl)-pyridine or a pharmaceutically acceptable salt thereof at a concentration of about 0.1 mg/ml to 2 mg/ml; and
b. a diluent, an excipient or a carrier suitable for a nasal administration comprising methylcellulose at a concentration of 0.5% by weight to 1% by weight based on a total weight of the composition.

Other general aspects of the invention relate to use of a pharmaceutical composition comprising a nicotinic acetylcholine receptor (nAChR) agonist and at least one pharmaceutically acceptable diluent, excipient, or carrier in the manufacture of a medicament for treating or preventing a condition of a nasal or paranasal mucous membrane in a subject; and a pharmaceutical composition comprising a therapeutically effective amount of a nicotinic acetylcholine receptor (nAChR) agonist and at least one pharmaceutically acceptable diluent, excipient, or carrier for use in a method of treating or preventing a condition of a nasal or paranasal mucous membrane in a subject in need thereof.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which have been included in the present specification is for the purpose of providing context for the invention. Such discussion is not an admission that any or all of these matters form part of the prior art with respect to any inventions disclosed or claimed.

Unless otherwise defined, all technical and scientific terms used herein have the same meaning as commonly understood to one of ordinary skill in the art to which this invention pertains. Otherwise, certain terms used herein have the meanings as set forth in the specification. It must be noted that as used herein and in the appended claims, the singular forms "a," "an," and "the" include plural references unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

The present invention relates to the application of melanocortin receptor (MCR) and nicotinic acetylcholine receptor (nAChR) agonists to human nasal and paranasal mucous membranes to treat or prevent conditions of the nasal and paranasal mucous membranes.

The inventor has surprisingly discovered that low doses of the nAChR agonist, such as (S)-(1-methyl-2-pyrrolidinyl)-pyridine, or a pharmaceutically acceptable salt, analog, precursor, or derivative thereof applied to the nasal and/or paranasal mucous membranes, preferably by topical application directly to the mucosal membranes, provides effective prophylactic and/or therapeutic treatment of conditions of the nasal and/or paranasal mucous membranes. Without wishing to be bound by any theories, it is believed that the application of the nAChR agonist, such as (S)-(1-methyl-2-pyrrolidinyl)-pyridine, to the mucous membranes of the nose stimulates and/or induces an increased secretion, release, mobilization, modulation and/or utilization of alpha melanocyte stimulating hormone (alpha-MSH), which in turn provides benefits as detailed below. In addition, the inventor has also discovered that photo-exposure or phototherapy with sunlight has been found to further improve the effectiveness of the nAChR agonist, such as the (S)-(1-methyl-2-pyrrolidinyl)-pyridine, applied to nasal and/or paranasal mucous membranes together with the consequent actions and benefits associated with alpha-MSH.

In one general aspect, the invention provides a method of treating or preventing a nasal or paranasal mucous membrane, or symptom thereof in a subject. The method comprises administering to the nasal or paranasal mucous membrane of the subject a therapeutically effective amount of a pharmaceutical composition comprising a nicotinic acetylcholine receptor (nAChR) agonist and at least one pharmaceutically acceptable diluent, excipient, or carrier.

As used herein, "subject" means any animal, preferably a mammal, most preferably a human, to whom will be or has been administered a pharmaceutical composition according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably a human.

The phrase "pharmaceutically acceptable salt" as used herein means those salts of a compound of interest that are safe and effective for pharmaceutical use in mammals and that possess the desired biological activity. Pharmaceutically acceptable salts include base addition salts, which are salts of basic groups present in the specified compounds, and acid addition salts, which are salts of acid groups present in the specific compounds. The acidic or basic groups can be organic or inorganic. For a review on pharmaceutically acceptable salts see Berge et al., 66 *J. PHARM. SCI.* 1-19 (1977), incorporated herein by reference.

As used herein, the term "pharmaceutical composition" is intended to encompass a product or composition comprising an active pharmaceutical ingredient in a therapeutically effective amount and a pharmaceutically acceptable carrier, diluent, or excipient. According to embodiments of the invention, an active pharmaceutical ingredient is a nicotinic acetylcholine receptor (nAChR) agonist. Examples of nAChR agonists suitable for use in the invention include, but are not limited to (S)-(1-methyl-2-pyrrolidinyl)-pyridine, (R)-(1-methyl-2-pyrrolidinyl)-pyridine, or a mixture thereof or a pharmaceutically acceptable salt, analog, precursor or derivative thereof; and acetylcholine. 1-methyl-2-pyrrolidinyl-pyridine is also referred to as nicotine; (S)-1-methyl-2-pyrrolidinyl)-pyridine is also referred to as (S)-nicotine; and (R)-(1-methyl-2-pyrrolidinyl)-pyridine is also referred to as (R)-nicotine.

Analogs of (S)-(1-methyl-2-pyrrolidinyl)-pyridine include compounds that structurally mimic (S)-(1-methyl-2-pyrrolidinyl)-pyridine, such as ABT-418 (Abbott). Precursors of (S)-(1-methyl-2-pyrrolidinyl)-pyridine include compounds that metabolize to produce (S)-(1-methyl-2-pyrrolidinyl)-pyridine, such as methylamine, glycine, acetic acid, and glucose.

Derivatives of (S)-(1-methyl-2-pyrrolidinyl)-pyridine include, but are not limited to anabaseine, anatalline, N-Benzyl-N-methylputrescine, butyl triacontonoate, cotinine, cotinine carboxylic acid methyl ester, cotinine perchlorate, 3-(4,5-dihydro-1-methyl-1H-pyrrol-2-yl)pyridine; 3(-3-pyridoyl)-2-(3H)-furanone, ethyl 4-oxo-4-(-3-pyridyl)butanoate, ethyl nicotinate-2,4,5,6,-d4; (R, S)—N-ethylnornicotine, N-formylnornicotine, guvacoline hydrobromide, isonicoteine, 2-hydroxyimino-4-methylnitrosamino-1-(3-pyridyl)-1-butanone, 5-hydroxyimino-5-(3-pyridyl)-pentanoic acid ethyl ester; N-(hydroxymethyl)nicotinamide, isonicoteine-3,4,5,6-d4, isonicotinamide-2,3,5,6-d4, isonicoteine, isonicotinic-d4 Acid, isonicotinoyl-d4 hydrazide, metanicotine, 1-(4-methoxybenzyl)-3-hydroxy-4-ethoxycarbonyl-5-(3-pyridyl)-3-pyrrolin-2-one, cis-1-(4-methoxybenzyl)-3-hydroxy-5-(3-pyridyl)-2-pyrrolidinone, (S)-1-methyl-d3-nicotinium iodide, 4-(methyl-d3-nitrosamino)-1-(3-pyridyl)-1-butanol, [methyl-d3]metanicotine, 1-methyl-3-(hydroxy-(3-pyridyl) methyl) pyrrolidine, (R,S)-1-Methyl-3-nicotinoylpyrrolidine, (R,S)-1-methyl-3-nicotinoylpyrrolidone, methyl 5-methylnicotinate, 2-methyl-6-(3-pyridyl)tetrahydro-1,2-oxazine, methyl 6-methylnicotinate, 2-methyl-6(S)-(3-pyridyl)tetrahydro-1,2-oxazine, 5-methyl myosmine, 4-(N-methyl-N-nitrosamino)-4-(3-pyridyl)butane-1-ol, 4-(N-methyl-N-propenylamino)-1-(3-pyridyl)-1-butanol, methyl nicotinate-2,4,5,6-d4, 5-methyl nornicotine, 4-(methylamino)-1-(3-pyridyl)-1-butanol, 4-(methylamino)-4-(3-pyridyl)butyric acid, N-methylbutane-1,4-diamine DiHCl, methylmetanicotine, (+/−)-2-methylnicotine; (+/−)-6-methylnicotine, 5-methylnicotine-d3; (S)-1-methylnicotinium iodide, 4-(methylnitrosamino)-1-(3-pyridyl-N-oxide)-1-butanol, 4-(methylnitrosamino)-1-(3-pyridyl-N-oxide)-1-butanone, 4-(methylnitrosamino)-1-(3-pyridyl)-1-butanol, 4-(methylnitrosamino)-1-(3-pyridyl)-1-butanone, 5-(methylnitrosamino)-1-(3-pyridyl)-1-pentanol, 5-(methylnitrosamino)-1-(3-pyridyl)-1-pentanone, 4-(methylnitrosamino)-4-(3-pyridyl)butyric acid, 1-methylpyrrolidinone-5,5-d2, myosmine, o-myosmine, nicotelline, nicotin-d3, nicotinamide-2,4,5,6-d4, nicotine-2,4,5,6-d4 (pyridine-d4), (+/−)-nicotine-d3 (N-methyl-d3), (+/−)-nicotine-d7 (N-methyl-d3, pyridine-d4), o-nicotine, (+/−)-nicotine-1,2', 3',4',5',6'-13C6, (+/−)-trans-nicotine-1'-oxide-methyl-d3, rac-trans-nicotine-1'-oxide, rac-trans-nicotine-1'-oxide-d3, (+/−)-nicotine-3'-d3, (S)-nicotine-5-carboxaldehyde, nicotine ditartrate dihydrate, (−)-nicotine mono tartrate, nicotine N-D-glucoside, nicotine N-D-glucoside 2,3,4,6-tetraacetate bromide HBr, nicotine salicylate, 3-(nicotinoyl-2,4,5,6-d4)-2-pyrrolidinone, nicotinuric acid-d4, N-nitroso-di-(n-butyl-d9)amine, N-nitroso-di-n-butylamine, N-nitroso-di-n-hexylamine, N-nitroso-N-ethylaniline, N-nitroso-N-methyl-3-aminopropionic Acid, N-nitroso-N-methyl-3-aminopropionic acid methyl ester, N-nitroso-N-methyl-4-aminobutyric acid, N-nitroso-N-methyl-4-aminobutyric acid methyl ester, N-nitroso-N-methylaniline, N-nitroso-N-methylurea, (S)—N-nitrosoanabasine, (R,S)—N-nitrosoanabasine D-glucoside chloride, (R,S)—N-nitrosoanatabine, N-nitrosodi-n-hexylamine, N-nitrosoguvacoline, nitrosonornicotine-2,4,5,6-d4 (pyridine-d4), rac N'-nitrosonornicotine-d4, rac N''-nitrosonornicotine-d4, rac N'''-nitrosonornicotine-d4 with (R,S)—N-Nitroso Anabasine-d4 (1:1), (R,S)-nornicotine bitartrate, 2-[3-oxo-3-(3-pyridyl)propyl]-1,3-dioxolane, γ-oxo-3-pyridinebutyric acid, γ-oxo-3-pyridinebutyric acid, N-hydroxysuccinimide ester; 1-(3-pyridyl)-1,4-butanediol; 1-(3-pyridyl)-1-butanol-4-carboxylic acid, ammonium salt; and solanesol.

Preferably, the nAChR agonist is (S)-(1-methyl-2-pyrrolidinyl)-pyridine, or a pharmaceutically acceptable salt thereof, and more preferably is (S)-(1-methyl-2-pyrrolidinyl)-pyridine. In a particularly preferred embodiment, aqueous(S)-(1-methyl-2-pyrrolidinyl)-pyridine having a purity of at least 98% purity is used. Aqueous (S)-(1-methyl-2-pyrrolidinyl)-pyridine can be purchased from a commercial source, such as Sigma. However, any synthetic nAChR agonist known to those skilled in the art in view of the present disclosure can be used in the invention.

As used herein, a "therapeutically effective amount" refers to an amount of a therapeutically active ingredient needed to elicit the desired biological or clinical effect. In one embodiment of the invention, a "therapeutically effective amount" is the amount of an nAChR agonist, such as (S)-(1-methyl-2-pyrrolidinyl)-pyridine, or a pharmaceutically acceptable salt, analog, precursor, or derivative thereof, needed to treat a condition of the nasal or paranasal mucous membrane. A "therapeutically effective amount" also refers to an amount that that has a prophylactic effect, i.e., prevents or delays the onset of a disease, disorder, or condition. In another embodiment of the invention, a "therapeutically effective amount" is the amount of an nAChR agonist, such as (S)-(1-methyl-2-pyrrolidinyl)-pyridine, or a pharmaceutically acceptable salt, analog, precursor, or derivative thereof, needed to prevent a condition of the nasal or paranasal mucous membrane. Methods are known in the art for determining the therapeutically effective amount of an active pharmaceutical ingredient according to embodiments of the present invention. Furthermore, and as is also understood by those of ordinary skill in the art, specific dose levels for any particular subject can vary depending upon a variety of factors including the age, body weight, general health, sex, diet, time of administration, route of administration, rate of excretion, any additional therapeutic agents administered in combination therewith and the severity of the disease, disorder, or condition to be treated or prevented.

As used herein, the terms "treat," "treating," and "treatment" refer to administering a therapeutically effective amount of an nAChR agonist, such as (S)-(1-methyl-2-pyrrolidinyl)-pyridine, or a pharmaceutically acceptable salt, analog, precursor, or derivative thereof, in order to reduce, alleviate, or slow the progression or development of a condition of the nasal or paranasal mucous membrane. In another embodiment, "treat," "treating," and "treatment" refer to reducing, slowing the progression of, or ameliorating one or more signs or symptoms of a condition of the nasal or paranasal mucous membrane. In particular embodiments of the invention, "treat," "treating," and "treatment" refer to reducing or inhibiting nasal congestion (chronic or acute) and/or associated headaches; and cessation of nasal hemorrhages (nose bleeding) and/or dryness of the nasal mucosa.

As used herein, the terms "prevent," "preventing," and "prevention" refer to administering a therapeutically effective amount of an nAChR agonist, such as (S)-(1-methyl-2-pyrrolidinyl)-pyridine, or a pharmaceutically acceptable salt, analog, precursor, or derivative thereof, before the onset of a condition of the nasal or paranasal mucous membrane, such that the condition of the nasal or paranasal mucous membrane is prevented altogether, time-delayed as to its occurrence, or still occurs, but to a lesser extent, than in the absence of administration of an nAChR agonist, such as (S)-(1-methyl-2-pyrrolidinyl)-pyridine, or a pharmaceutically acceptable salt, analog, precursor, or derivative thereof. In particular embodiments of the invention, "prevent," "preventing," and "prevention" refer to inhibiting or slowing the onset of development or progression of nasal congestion (chronic or acute) and/or associated headaches; and cessation of nasal hemorrhages (nose bleeding) and/or dryness of the nasal mucosa.

As used herein, the phrase "a condition of a nasal or paranasal mucous membrane" refers to any disease, disorder, or condition that affects the mucous membranes of the nasal cavity and paranasal sinuses. The nasal mucosa, or mucous membrane, is a type of usually moist tissue that lines the nasal cavity. The paranasal sinuses are a group of four paired air-filled spaces that surround the nasal cavity. The paranasal mucosa or mucous membrane is a type of tissue that lines the paranasal sinuses. Conditions of the nasal/paranasal mucous membranes can also affect other parts of the nasal cavity and areas surrounding the nasal cavity and paranasal sinuses, including but not limited to the nasal cartilage and vomer. The vomer is the unpaired facial bones of the skull that form the inferior part of the nasal septum. Thus, a condition of a nasal or paranasal mucous membrane also includes diseases and conditions that affect other parts of the nasal cavity and areas surrounding the nasal cavity and paranasal sinuses, such as the nasal cartilage and vomer.

Examples of conditions of a nasal or paranasal mucous membrane include, but are not limited to, nasal congestion; rhinitis; allergic rhinitis; acute rhinitis; atrophic rhinitis; vasomotor rhinitis; chronic or recurrent sinusitis; an inflammation, a chronic inflammatory disease, or an acute inflammatory disease of the structures of the nose and surrounding tissues; hemorrhages; minor bleeding; a chronic degenerative disease; an acute degenerative disease; edema of the mucous membranes; edema of one or more turbinates; turbinate hypertrophy (enlarged turbinates); Sjögren syndrome (dry syndrome of nasal mucosa); rhinitis induced by stress; secondary reactions or side effects to systemic medications; and pre-cancerous and cancerous changes of the nasal mucosa. Other examples of a nasal or paranasal mucous membrane include, but are not limited to, postnasal drainage; facial pressure and pain; headaches; dripping of mucous membrane secretions down the throat; post nasal drip; a runny nose from the nares (nostrils); abnormal taste sensations; feeling of dryness in the upper respiratory tract; drowsiness; nasal irritation; a loss of the sense of smell; burning sensations within the nose; ear or hearing issues; itchy nose; itchy eyes; watering eyes; sneezing; a stuffed nose; snoring; sleep apnea; asthma; nasal polyps (nasal polyposis); exposure to environmental irritants or allergens; stress, atopic diseases, and rheumatoid arthritis.

According to embodiments of the invention, a condition of a nasal or paranasal mucous membrane also includes co-morbidities and/or associated conditions. Co-morbidities and conditions associated with the nasal and paranasal mucous membranes include, but are not limited to, snoring, sleep apnea, asthma and nasal polyps (nasal polyposis). Treatment of these co-morbidities and associated conditions using the methods of the invention may be due to the improvement in the physiology of the nose from the use or application of the invention. As described in detail below the increased stimulation of secretion of alpha-MSH is believed to beneficially improve the energy levels of formerly pathologic cells within or associated with the nose.

With respect to treatment of pre-cancerous and cancerous cells, it is believed that the stimulated release of alpha-MSH by the invention may revert or restore the cancerous cells to a more normal state rather than kill them. For example, in experimental cultures of human cancer cells, administration of (S)-(1-methyl-2-pyrrolidinyl)-pyridine, at concentration of 5 mg/ml, inhibits proliferation by 95%.

In preferred embodiments of the invention, the condition of the nasal or paranasal mucous membrane is chronic nasal congestion or nasal hemorrhages ("nose bleeds"). For example, nasal hemorrhages or "nose bleeds" may be arrested or alleviated more quickly with the use of the invention.

According to embodiments of the invention, the application of the invention to the nose can also have a beneficial therapeutic effect beyond the nose, such as, relief to rheumatoid arthritis and other inflammatory, degenerative or infectious conditions.

Without wishing to be bound by any theories, the anatomy, function and general physiology of the nose and associated mucous membranes may be improved and restored with the use of the invention and as discussed in detail below with respect to alpha-MSH. In addition, disease conditions of the nasal cartilage and/or the vomer (nasal bone to the nasal septum) can also be improved or restored with the use of the invention.

Pharmaceutical Composition and Preparation Thereof

A pharmaceutical composition used in the methods of the invention comprises a nicotinic acetylcholine receptor (nAChR) agonist and at least one pharmaceutically acceptable diluent, excipient, or carrier. Any diluent, excipient, or carrier known to those skilled in the art in view of the present disclosure can be used. Preferably, the diluent, excipient, or carrier is suitable for nasal administration. Non-limiting examples of diluents, excipients, and/or carriers suitable for use with the invention include water; thickening or viscosity increasing agents; and preservatives. For example, the nAChR agonist, such as (S)-(1-methyl-2-pyrrolidinyl)-pyridine, can be combined with an aqueous (water) based vehicle or an excipient suitable for pharmaceutical use in humans and/or animals. Any of the pharmaceutical compositions described herein can be used in the methods of the invention.

According to embodiments of the invention, a pharmaceutical composition for use in the invention is suitable for nasal administration. Examples of compositions suitable for nasal administration include, but are not limited to, aqueous solutions, ointments, and gels. A composition suitable for nasal administration can be administered topically (e.g., ointment or gel), as a nasal spray or using an aerosol delivery mechanism (e.g., inhaler), or as drops (e.g., aqueous solution). One of ordinary skill in the art would know how to prepare such compositions using conventional techniques in the art.

In other embodiments, an nAChR agonist, such as (S)-(1-methyl-2-pyrrolidinyl)-pyridine, can also be suitably prepared in a nasal drug delivery composition as a fine or colloidal particulate suspension in an aqueous solvent. In yet other particular embodiments, an nAChR agonist, such as (S)-(1-methyl-2-pyrrolidinyl)-pyridine, can be combined with another excipient or vehicle to form an ointment or a gel. The use of the ointment or the gel as a nasal drug delivery composition allows for direct topical application of the ointment or the gel to mucous membranes of specific parts of the nasal cavity or paranasal sinuses.

In a preferred embodiment of the invention, the pharmaceutical composition is an aqueous composition, preferably suitable for nasal administration via drops.

A pharmaceutical composition can comprise the nAChR agonist in a concentration of about 0.1 mg/ml to 2.0 mg/ml, such as 0.1 mg/ml, 0.2 mg/ml, 0.3 mg/ml, 0.4 mg/ml, 0.5 mg/ml, 0.6 mg/ml, 0.75 mg/ml, 1.0 mg/ml, 1.25 mg/ml, 1.5 mg/ml, 1.75 mg/ml, or 2.0 mg/ml. In one illustrative example of the invention, a pharmaceutical composition comprises (S)-(1-methyl-2-pyrrolidinyl)-pyridine at a concentration of about 0.1 mg/ml to 2.0 mg/ml, such as 0.1 mg/ml, 0.2 mg/ml, 0.3 mg/ml, 0.4 mg/ml, 0.5 mg/ml, 0.6 mg/ml, 0.75 mg/ml, 1.0 mg/ml, 1.25 mg/ml, 1.5 mg/ml, 1.75 mg/ml, or 2.0 mg/ml. A preferred concentration of about 0.75 mg/ml of (S)-(1-methyl-2-pyrrolidinyl)-pyridine in an aqueous solution can also be used. Alternatively, concentrations in a range of about 0.1 mg/ml to 0.5 mg/ml to can be used for surprisingly very low doses, yet still have a therapeutic effect. Concentrations higher than 2 mg/ml are typically undesirable for nasal application, as it may be irritating to the patient and reduce compliance to the prescribed therapy for successful treatment. For example, the patient may experience itching in the nose and other side effects common to those using nasally applied smoking cessation therapies. An alternative to a higher concentration is the use of more frequent dosing. Increased dosing may be desirable for situations where there is, for example, a lack of response due to a severity or a chronic nature of the initial symptoms and as described further below. Dosing is described further in detail below.

In certain embodiments, a thickening or viscosity increasing agent can also be added to the pharmaceutical composition to improve the retention or otherwise adherence of the nAChR agonist solution, such as an aqueous solution of (S)-(1-methyl-2-pyrrolidinyl)-pyridine, to the mucous membranes that it is applied to. The viscosity increasing agent is used at such a sufficient concentration and appropriate formulation to enable the composition to remain localized to a mucous membrane site for a sufficient period, such that a sufficient therapeutic dose from the active ingredient, e.g., (S)-(1-methyl-2-pyrrolidinyl)-pyridine, is imparted to the mucous membrane. Examples of thickening or viscosity increasing agents that can be used with the invention include methylcellulose. In another alternative, suitably formulated cacao fat or cacao butter compounds can be used to increase the viscosity of an aqueous solution. It will be readily appreciated that other compounds which are non-allergenic and otherwise suitable for nasal use can be used to increase the viscosity and adherence to nasal mucosa of a pharmaceutical composition for use in the invention.

In a preferred embodiment, methylcellulose is used to increase the viscosity of a pharmaceutical composition used in the invention, such as an aqueous solution. A concentration of methylcellulose sufficient to increase the viscosity of a pharmaceutical composition, such as an aqueous solution of (S)-(1-methyl-2-pyrrolidinyl)-pyridine, can be about 0.5% by weight to 1% by weight, such as 0.5%, 0.6%, 0.7%, 0.8%, 0.9%, or 1% by weight based on a total weight of the composition.

In other embodiments, a preservative can be added to the pharmaceutical composition. As an illustrative an non-limiting example, salicylic acid can be used as the preservative. For example, a pharmaceutical composition for use in the invention can comprise salicylic acid in a concentration of 0.1 mg/ml to 1 mg/ml, such as 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In particular embodiments, a pharmaceutical composition for use in the invention further comprises about 0.5 mg/ml of salicylic acid.

Application to the Nose

According to embodiments of the invention, a pharmaceutical composition is administered to the nasal or paranasal mucous membrane of the subject. Any method known in the art in view of the present disclosure can be used for administration to the nasal or paranasal mucous membrane. Preferably, the pharmaceutical composition is administered nasally, such as by drops, nasal aerosol spray, ointment or gel.

In particular embodiments, an (S)-(1-methyl-2-pyrrolidinyl)-pyridine aqueous solution can be administered by the application of drops to the nasal cavity via the nares (nostrils). Alternatively, an (S)-(1-methyl-2-pyrrolidinyl)-pyridine aqueous solution can be used in a nasal spray or an aerosol delivery mechanism and apparatus, such that the nicotine aqueous solution is sprayed in a single or multiple shot wise fashion. In yet another embodiment, a pharmaceutical composition, such as a gel or ointment, can be administered nasally by topical application to one or more mucous membranes of the nasal cavity of a superior turbinate, a middle turbinate and an inferior turbinate olfactory bulbs; and/or one or more mucous membranes of the paranasal sinuses of a frontal sinus, a sphenoid's sinus, a maxillary sinus and an ethmoid sinus.

As an illustrative and non-limiting example, an aqueous pharmaceutical composition comprising (S)-(1-methyl-2-pyrrolidinyl)-pyridine in the concentration range detailed above is administered nasally. One to two drops (about 0.05 ml per drop) of the composition for a single treatment can be administered to the patient via one or both nostrils while the patient is lying down. In typical embodiments, one drop is administered in each nostril. Immediately after the placement of the drops in the nose, the patient can be instructed to inhale as forcefully as possible or as appropriate for their condition to give adequate exposure of the mucous membranes to the (S)-(1-methyl-2-pyrrolidinyl)-pyridine. An ordinary dropper can be used to apply the drops within the nostrils or nares, although for some patients it may be desirable to use a narrow and/or elongated dropper or a catheter to place the drops deeper within the nasal cavity. Rotation and/or inversion of the patient's head during application of the (S)-(1-methyl-2-pyrrolidinyl)-pyridine nasal drug may also be desirable. For example, for patients with difficult to access areas of nasal congestion in the nasal cavity or for which a high degree penetration to the paranasal sinuses is desirable, rotation and/or inversion of the patient's head may be preferable. After the drops of (S)-(1-methyl-2-pyrrolidinyl)-pyridine are applied, the patient may be instructed to rotate their head side-to-side and/or tilt their head backwards and forwards until it is felt by the patient or the clinician that (S)-(1-methyl-2-pyrrolidinyl)-pyridine drops have travelled in part at least to the desired location of the nasal cavity and/or the paranasal sinuses.

The application of a pharmaceutical composition according to a method of the invention in cases of initial severe nasal congestion can also be aided by administering to the patient initial means for temporarily relieving nasal congestion as are commonly already available. The subsequent administration of (S)-(1-methyl-2-pyrrolidinyl)-pyridine, for example, may then be able to more effectively penetrate the nasal cavity and paranasal sinuses. However, it is generally found that even in cases of chronic nasal congestion, (S)-(1-methyl-2-pyrrolidinyl)-pyridine as used in the invention is surprisingly fast and effective in penetrating and dosing to the desired mucous membranes.

The frequency of administration and dosing regimen will vary according to patient, condition to be treated or preventing, the severity of the condition, etc. For example, the frequency of administration or dosing regimen for an aqueous solution of (S)-(1-methyl-2-pyrrolidinyl)-pyridine can be one to two drops. The drops can be administered once daily, or more than once daily such as two to four times a day. Typically, a "drop" has a volume of about 0.01 ml to 0.1 ml, such as 0.01, 0.02, 0.03, 0.04, 0.05, 0.06, 0.07, 0.08, 0.09, or 0.1 ml. By way of example, one to two drops of an aqueous solution containing 0.01 mg/ml to 0.1 mg/ml of (S)-(1-methyl-2-pyrrolidinyl)-pyridine, with each drop having a volume of about 0.05 ml, can be administered to a patient two to four times daily for a daily dose of (S)-(1-methyl-2-pyrrolidinyl)-pyridine of about 0.01 mg to 0.4 mg. Such very low, daily doses of (S)-(1-methyl-2-pyrrolidinyl)-pyridine are typically at least an order of magnitude (×10) less than that used with smoking cessation aids, for example M. Bende et al, *"Evaluation of side effects after nicotine nasal spray in patients with chronic rhinitis"*, Rhinology, 36, 98-100, 1998, the contents of which are incorporated herein by reference. The very low doses also allow for prolonged treatment periods extending to many months, surprisingly without adverse effects. The prolonged period of therapeutic application is believed to allow for restorative processes within the nose to occur due to an increased secretion of alpha-MSH as described herein. Furthermore, the very low doses of (S)-(1-methyl-2-pyrrolidinyl)-pyridine together with localization of the treatment to the nasal cavity and paranasal sinuses are surprisingly beneficial and advantageous to the patient in comparison to systemic alternative medications for nasal congestion, which inherently require dosing to the entire body.

The treatment, such as treatment with a nasally administered an aqueous solution of (S)-(1-methyl-2-pyrrolidinyl)-pyridine can be continued indefinitely or tapered according to the individual patient's response and clinical supervision. As a general comment, the improvement experienced by each patient is often surprisingly remarkable and rapid. The improvements are generally observed within one to two days to a week. For patients where the initial cause of, e.g., nasal congestion in their environment is now absent or who have reduced the use of (S)-(1-methyl-2-pyrrolidinyl)-pyridine aqueous solution, can stop treatment after a few weeks or months, with perhaps sporadic follow-up use if nasal congestion symptoms should flare up again. Those patients with chronic nasal congestion due to environmental causation agents or other factors may require treatment with the very low and localized dose of (S)-(1-methyl-2-pyrrolidinyl)-pyridine aqueous solution to be continued for many months, years or indefinitely. For example, those patients with nasal congestion induced or caused by environmental factors as extreme cold, dust or particulates, air pollution, cigarette smoke, seasonal allergens such as pollens and the like, may require long term use of (S)-(1-methyl-2-pyrrolidinyl)-pyridine aqueous solution.

In determining the success of the application of the invention and adjusting the effective dosing regimen and/or effective treatment regimen, the inventor has found that a restoration or at least a significant improvement in the normal secretion and ciliary function of the mucous membranes in the nasal cavity and the paranasal sinuses may provide the best guide for a therapeutically effective dose and/or treatment regimen. Improvements in the function of the mucous membranes can be reported by the patient and/or as observations by the clinician treating the patient.

Application of (S)-(1-methyl-2-pyrrolidinyl)-pyridine nasal drug and consequent improvements to mucous membranes located in the nasal cavity can be directly seen for the multiple nasal turbinates of the superior turbinate, the middle turbinate and/or the inferior turbinate with the appropriate viewing device or apparatus for inserting into the nasal cavities. For example, a rhinoscopy examination with an endoscope or by dilating the nostrils and viewing directly the turbinates can be used to evaluate improvements to the mucous membranes. In addition, mucous membranes about the olfactory bulbs in the nasal cavity can also be improved. For the paranasal sinuses, the mucous membranes located in the frontal sinus, sphenoidal sinus, maxillary sinuses and/or ethmoidal air cells/ethmoid sinus can also benefit from the application of the nicotine nasal drug.

Follow-up examinations and biopsies of the mucous membranes, for example nasal cytology studies, can be performed to assess improvement in the cytology of nasal tissues. However, patient and clinician reports are often sufficient, as nasal cytology studies for example may be insensitive to significant functional changes noticed by the patient and/or clinician. Mucous membrane cells that may respond most favorably to the application of a pharmaceutical composition comprising an nAChR agonist, particularly (S)-(1-methyl-2-pyrrolidinyl)-pyridine include goblet cells, squamous cells, columnar epithelial cells and ciliated cells as well as other cells located in the nose. In addition other cell populations within the mucous membrane and elsewhere in the body that have nAChRs, such as (S)-(1-methyl-2-pyrrolidinyl)-pyridine receptors and/or either secrete or are associated with the secretion of alpha-MSH may also respond to treatment according to the methods of the invention, as discussed in detailed below.

It will also be readily appreciated by one of ordinary skill in the art that in addition to the treatment protocols described above, an effective treatment and an effective dosing regimen applied to a patient may also depend on the patient's age, sex, height, weight, previous health state, alcohol intake for example. One of ordinary skill in the art will be readily able to determine the appropriate dosing regimen, amount for administration, etc. in order to achieve the desired therapeutic result for a particular patient in view of the present disclosure.

In certain embodiments of the invention, a subject is further treating with a phototherapy. Examples of phototherapy suitable for use with the invention include, but are not limited to, exposure to sunlight. The inventor has also found the surprising and unexpected result that some photoexposure or phototherapy with sunlight or other visible light to the patient further improves the results obtained with the (S)-(1-methyl-2-pyrrolidinyl)-pyridine nasal drug. Visible light can be in the approximate range of 380 to 780 nm. The light used can be from sunlight or artificial sources made by man.

Alternatively, the subject can be treated with other energy sources, such as ultraviolet light or radiation; infrared light or radiation; magnetic fields; sound including audible and ultrasonic waves; electromagnetic radiation, etc. Ultra-violet light or radiation can be in the approximate ranges of 315 to 400 nm for ultraviolet-A (UVA) and approximately 280 to 315 nm for ultraviolet-B (UVB) as well as an overall approximate range of 380 to 280 nm. Infrared light or radiation can be used in the approximate range of 730 nm to 1 mm. The proposed mechanism of the further improvement observed with photoexposure or phototherapy, or treatment with other energy sources is described in detail below.

It has been found that individual patients may report that a sufficient dose of sunlight is received with an improved feeling of well-being. It has been observed that approximately half an hour to two hours walk in sunlight may be sufficient. Other patients may achieve the same effect by sitting in sunshine for a similar period of time. Alternatively, the patient may sit in the shade of a verandah, conservatorium, tree or the like to receive indirect sunlight. It will be readily appreciated that the level of light exposure for a particular patient may vary with their racial type, skin pigmentation, amount of skin exposed to the light, the intensity of the light, as well as the particular condition being treated. It will also be appreciated that the patient may have diagnostic tests for the level of alpha-MSH secreted and/or tests of their nasal mucous membranes to enable a sufficient amount of light to be determined.

Without wishing to be bound by any theories, the mechanism by which administration of nAChR agonists, such as (S)-(1-methyl-2-pyrrolidinyl)-pyridine, exert their therapeutic effects is believed to be through inducing or stimulating a release of alpha-MSH (alpha-melanocyte stimulating hormone), as described in PCT Patent Application Publication WO2007129879 and U.S. Patent Application Publications U.S. 2012270907 and U.S. 2009197921, which are herein incorporated by reference in their entireties. The same or similar mechanism proposed for the therapeutic effects observed in other parts of the body with increased secretion of alpha-MSH may also apply to the therapeutic effects observed in one or more mucous membranes located in the nasal cavity and/or paranasal sinuses in response to the application of a pharmaceutical composition comprising an nAChR agonist, such as (S)-(1-methyl-2-pyrrolidinyl)-pyridine as described herein.

Briefly, alpha-MSH is a tridecapeptide endogenous hormone derived from propiomelanocortin that is expressed in several regions of the central nervous system and in peripheral cells, melanocytes, phagocytes, macrophages, chrondrocytes, keratocytes, glial cells, keratinocytes, skin cells and pilose follicles, etc. In addition, the mucous membrane cells of the nasal cavity and paranasal sinuses may also express or secrete alpha-MSH. Alpha-MSH has anti-inflammatory effects, mainly through the antagonism of pro-inflammatory mediators including α-Tumor Necrosis Factor, interleukin 6 (IL-6) and nitric oxide (NO). Alpha-MSH may also have strong effects in all tissues.

The mechanism of action of alpha-MSH is extensive, which the inventor believes can be explained by an increase in the generation of chemical energy from melanin in the form of molecular hydrogen and high energy electrons. This process has many physiological effects, such as inhibiting inflammation, inhibiting cytotoxic effects, and inhibiting apoptotic pathways activated by renal ischemia. It is also believed that the administration of nicotine to a patient may also induce and/or increase the secretion of alpha-MSH from the melanotrophs located in the pars intermedia of the hypophysis (pituitary gland) in close contact or association with mammotrophs. The release of alpha-MSH may provoke "photosynthesis" in a human patient and/or animal by causing an increase in the synthesis of melanin. The melanin in turn can increase release or availability of oxygen and hydrogen into the tissue from water, as described in PCT Patent Application Publication WO2007129879 and U.S. Patent Application Publications U.S. 2012270907 and U.S. 2009197921, which are herein incorporated by reference.

The use of the term "human photosynthesis" is a loose analogy to the process undertaken by plants of carbohydrate synthesis by combining carbon dioxide, water and sunlight in the presence of chlorophyll. The release of oxygen and hydrogen via melanin in the present application increases the energy available to a eukaryotic cell, particularly in the nasal and/or paranasal mucous membranes, further energizing many of the intracellular reactions. This additional source of energy may form a substantial part of a eukaryotic cell's energy requirements and provide a dramatic and positive growth or repair response in all tissues, including the surprising and unexpected result of a beneficial effect to the nasal and the paranasal mucous membranes.

Further details on the interactions between melanin and light are described in the journal article Gjumrakch Aliev et al., "Human photosynthesis, the ultimate answer to the long term mystery of Kleiber's law or $E=M^{3/4}$: Implication in the context of gerontology and neurodegenerative diseases" *Open Journal of Psychiatry*, 2013, 3, 408-421, the contents of which are incorporated herein by reference.

With respect to nasal and paranasal mucous membranes, topical application of (S)-(1-methyl-2-pyrrolidinyl)-pyridine, for example, to the nasal and paranasal mucous membranes may induce the release and/or increased secretion of alpha-MSH in many of the cells of the nasal and the paranasal membranes. As described above, many eukaryotic cells have nicotinic receptors and may synthesize and/or secrete alpha-MSH. Furthermore, the nasal and paranasal mucous membranes have a highly vascular blood supply, such that cells away from the nasal cavity and paranasal sinuses may be readily stimulated to release and/or increase secretion of alpha-MSH in response to (S)-(1-methyl-2-pyrrolidinyl)-pyridine introduced into the circulating blood plasma via the nasal route. That is, the nasal administration of (S)-(1-methyl-2-pyrrolidinyl)-pyridine may produce a localized and generalized response of increasing alpha-MSH levels in the body with consequent benefits as described herein.

(S)-(1-methyl-2-pyrrolidinyl)-pyridine in surprisingly very low doses, such as about 0.1 mg/ml to 2 mg/ml in an aqueous solution and applied topically to the nasal cavity and/or paranasal sinuses as described herein, may induce several processes in the nasal and/or paranasal membranes. One of the therapeutic responses is the intensification of the dissociation of the water molecule to hydrogen and oxygen as described above. The consequent reactions with oxygen and hydrogen are highly dependent on the very first dissociation reaction of the water molecule within the cells of the mucous membranes of the nasal cavity and/or paranasal sinuses. The consequent reactions with oxygen and hydrogen within the cells of the mucous membranes may provide increased energy to those cells in the therapeutic and prophylactic treatment of the disease conditions and symptoms described above.

In addition to the use of sunlight for photo-exposure and/or phototherapy, the inventor has also identified that visible light in the sunlight spectrum may be particularly beneficial as well as infrared light and ultraviolet light. The photo-exposure can induce or stimulate further alpha-MSH release as well as light interactions with melanin for energy release of oxygen and hydrogen from intracellular water as described above.

EXAMPLES

Clinical Examples

Example 1: Treatment of a Patient Having Chronic Nasal Congestion

A female patient aged 31 with chronic nasal congestion for the past 10 years. Prior treatments by multiple physicians had poor outcomes, including prior treatment with local and systemic vasoconstricors and antibiotics. An initial examination of the patient showed that her nasal cavity mucous membranes exhibited moderate edema. The right inferior turbinate was slightly enlarged and inflamed. The patient also complained of frequent headaches in the forehead region.

Treatment for the patient was begun with an aqueous solution containing (S)-(1-methyl-2-pyrrolidinyl)-pyridine at a concentration of 1.00 mg/ml and salicylic acid at a concentration of 0.5 mg/ml with a dose of two drops in each nostril (about 50 μL per drop), followed by inhalation. The dose was repeated three or four times a day. On a follow-up one month later, the patient reported that her symptoms had improved by 90%, with 100% being what the patient considered normal. The clinician recommended ongoing treatment with the (S)-(1-methyl-2-pyrrolidinyl)-pyridine aqueous solution with follow-ups for possibly up to a one year given the chronic initial presentation of the patient. It was felt by the clinician that the possible causative agent/s for the chronic nasal congestion may have been external environment factors such as cold, dust, air pollution, second-hand cigarette smoke and/or seasonal allergens such as pollens.

Example 2: Treatment of a Patient Having a History of Nose Bleeds and Dryness

The patient was a 68-year old female with a history of nose bleeding in small quantities and sensation of dryness in the nose and eyes. The patient also reported a long history of joint pain, but no other remarkable antecedents. The patient presented at examination with an atrophy of the nasal cavity mucous membranes, which was determined to not be recent.

The treatment for patient two began with an aqueous solution of (S)-(1-methyl-2-pyrrolidinyl)-pyridine at a concentration of 2.0 mg/ml and salicylic acid at a concentration of 0.5 mg/ml at a dose of one to two drops (about 50 μL per drop) followed by forced inhalation. The dose was repeated three to four times a day. On a follow-up visit one month later, the patient reported that nasal bleeding had ceased and the sensation of dryness in the nose and eyes had diminished markedly since the first week of treatment. The clinician recommended ongoing treatment with the (S)-(1-methyl-2-pyrrolidinyl)-pyridine aqueous solution with follow-up visits for possibly up to one year given the initial present of atrophied mucous membranes in the nasal cavity. The initial improvement was surprisingly rapid with respect to cessation of bleeding and relief to the sensation of dryness. The further regeneration or restoration of the atrophied mucous membranes will probably entail many months to possibly a few years of treatment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

Embodiments

Embodiment 1 is a method of treating or preventing a condition of a nasal or paranasal mucous membrane in a subject, the method comprising administering to the nasal or paranasal mucous membrane of the subject a therapeutically effective amount of a pharmaceutical composition comprising a nicotinic acetylcholine receptor (nAChR) agonist and at least one pharmaceutically acceptable diluent, excipient, or carrier.

Embodiment 2 is the method of embodiment 1, wherein administration of the pharmaceutical composition to the nasal or paranasal mucous membrane induces and/or stimulates a release of alpha-MSH.

Embodiment 3 is the method of embodiment 1, wherein the nAChR agonist is synthetic or natural (S)-(1-methyl-2-pyrrolidinyl)-pyridine, or a pharmaceutically acceptable salt, analog, precursor, or derivative thereof.

Embodiment 4 is the method of any one of embodiments 1-3, wherein the condition is selected from the group consisting of nasal congestion, rhinitis, allergic rhinitis, acute rhinitis, atrophic rhinitis, vasomotor rhinitis, chronic or recurrent sinusitis, an inflammation, a chronic inflammatory disease, an acute inflammatory disease, hemorrhages, minor bleeding, a chronic degenerative disease, an acute degenerative disease, edema of the mucous membranes and edema of one or more turbinates.

Embodiment 5 is the method of any one of embodiments 1-3, wherein the condition is selected from the group consisting of postnasal drainage, facial pressure and pain, headaches, dripping down the throat of mucous membrane secretions, post nasal drip, a runny nose from the nares or nostrils, abnormal taste sensations, dry feelings about the upper respiratory tract, drowsiness, nasal irritation, a loss of the sense of smell, burning sensations within the nose, ear or hearing issues, itchy nose, itchy eyes, watering eyes, sneezing and a stuffed nose; snoring, sleep apnea, asthma and nasal polyps (nasal polyposis), stress, atopic diseases, exposure to environmental irritants or allergens and rheumatoid arthritis.

Embodiment 6 is the method of any one of embodiments 1-5, wherein the pharmaceutical composition comprises (S)-(1-methyl-2-pyrrolidinyl)-pyridine at a concentration of about 0.5 mg/ml to 2.0 mg/ml.

Embodiment 7 is the method of any one of embodiments 1-5, wherein the pharmaceutical composition comprises (S)-(1-methyl-2-pyrrolidinyl)-pyridine at a concentration of about 0.1 mg/ml to 0.5 mg/ml.

Embodiment 8 is the method of embodiment 6 or 7, wherein the (S)-(1-methyl-2-pyrrolidinyl)-pyridine is in an aqueous solution.

Embodiment 9 is the method of any one of embodiments 1-8, wherein the diluent, excipient, or carrier comprises a thickening or viscosity increasing agent to sufficiently localize the nAChR agonist to one or more mucous membranes.

Embodiment 10 is the method of embodiment 9, wherein the diluent, excipient, or carrier comprises methylcellulose at a concentration of about 0.5% by weight to 1% by weight based on a total weight of the composition.

Embodiment 11 is the method of any one of embodiments 1-10, wherein the pharmaceutical composition is administered nasally.

Embodiment 12 is the method of any one of embodiments 1-11, wherein the pharmaceutical composition is administered by use of drops, a nasal aerosol spray, an ointment or a gel.

Embodiment 13 is the method of any one of embodiments 1-12, wherein the pharmaceutical composition is administered according to at least one of:
one or two drops in each nostril, and
repeated two to four times daily.

Embodiment 14 is the method of any one of embodiments 1-13, wherein the pharmaceutical composition is applied topically to one or more mucous membranes of the nasal cavity of: a superior turbinate, a middle turbinate and an inferior turbinate olfactory bulbs; and/or one or more mucous membranes of the paranasal sinuses of: a frontal sinus, a sphenoid's sinus, a maxillary sinus and an ethmoid sinus.

Embodiment 15 is the method of embodiment 2, wherein the inducing and/or stimulating of the release of alpha-MSH includes alpha-MSH released from melanotrophs located in a pars intermedia of a hypophysis of a human subject.

Embodiment 16 is the method of embodiment 2, wherein the inducing and/or stimulating of the release of alpha-MSH includes alpha-MSH from at least one of a population cells in the nasal mucous membrane of goblet cells, squamous cells, columnar epithelial cells and ciliated cells.

Embodiment 16 is the method of embodiment 2, wherein the inducing and/or stimulating of the release or secretion of alpha-MSH includes alpha-MSH from at least one population cells of a nose of: melanocytes, phagocytes, macrophages, chrondrocytes, keratocytes, glial cells, keratinocytes, skin cells, pilose follicles, cartilage cells, bone cells and stem cells.

Embodiment 17 is the method of any one of embodiments 1-16, further comprising treatment of the subject with a phototherapy.

Embodiment 18 is the method of embodiment 17, further comprising modulating a secretion of a melanin, wherein a melanin response induced by a phototherapy promotes one or more of a release of oxygen and hydrogen in a tissue.

Embodiment 19 is the method of embodiment 18, wherein the release of at least one of oxygen and hydrogen in tissue increases energy into a eukaryotic cell.

Embodiment 20 is a method of treating a condition of a nasal or paranasal mucous membrane in a human subject in need thereof, the method comprising nasally administering to the nasal or paranasal mucous membrane of the subject a therapeutically effective amount of an aqueous pharmaceutical composition comprising about 0.1 mg/ml to 2.0 mg/ml of (S)-(1-methyl-2-pyrrolidinyl)-pyridine or a pharmaceutically acceptable salt thereof and at least one pharmaceutically acceptable diluent, excipient, or carrier, wherein the condition is selected from the group consisting of nasal congestion and nasal hemorrhages ("nose bleeds").

Embodiment 21 is the method of embodiment 20, wherein the pharmaceutically acceptable carrier, diluent or excipient comprises methylcellulose at a concentration of 0.5% by weight to 1% by weight based on a total weight of the composition.

Embodiment 22 is the method of embodiment 20 or 21, wherein the pharmaceutical composition is administered by drops or a nasal aerosol spray.

Embodiment 23 is the method of any one of embodiments 20-22, wherein the pharmaceutically acceptable carrier, diluent or excipient comprises methylcellulose at a concentration of 0.5% by weight to 1% by weight based on a total weight of the composition.

Embodiment 24 is the method of any one of embodiments 20-23, wherein the aqueous pharmaceutical composition is administered in a dose of one or two drops per nostril with each drop having a volume of about 0.01 ml to 0.1 ml, and the administration is optionally repeated two to four times daily.

Embodiment 25 is a pharmaceutical composition comprising:
a. (S)-(1-methyl-2-pyrrolidinyl)-pyridine or a pharmaceutically acceptable salt, analog, precursor, or derivative thereof at a concentration of about 0.1 mg/ml to 2 mg/ml; and
b. a diluent, an excipient or a carrier suitable for a nasal administration.

Embodiment 26 is the pharmaceutical composition of embodiment 25, being an aqueous pharmaceutical composition.

Embodiment 27 is the pharmaceutical composition of embodiment 25 or 26, wherein the diluent, excipient, or carrier comprises methylcellulose at a concentration of 0.5% by weight to 1% by weight based on a total weight of the composition.

Embodiment 28 is use of a pharmaceutical composition comprising a nicotinic acetylcholine receptor (nAChR) agonist and at least one pharmaceutically acceptable diluent, excipient, or carrier in the manufacture of a medicament for treating or preventing a condition of a nasal or paranasal mucous membrane in a subject.

Embodiment 29 is use of an aqueous pharmaceutical composition comprising about 0.1 mg/ml to 2.0 mg/ml of (S)-(1-methyl-2-pyrrolidinyl)-pyridine or a pharmaceutically acceptable salt thereof and at least one pharmaceutically acceptable diluent, excipient, or carrier, in the manufacture of a medicament for treating a condition of a nasal or a paranasal mucous membrane in a human subject in need thereof, wherein the condition is selected from the group consisting of nasal congestion and nasal hemorrhages ("nose bleeds").

Embodiment 30 is a pharmaceutical composition comprising a therapeutically effective amount of a nicotinic acetylcholine receptor (nAChR) agonist and at least one pharmaceutically acceptable diluent, excipient, or carrier for use in a method of treating or preventing a condition of a nasal or paranasal mucous membrane in a subject in need thereof.

Embodiment 31 is an aqueous pharmaceutical composition comprising about 0.1 mg/ml to 2.0 mg/ml of (S)-(1-methyl-2-pyrrolidinyl)-pyridine or a pharmaceutically acceptable salt, analog, precursor, or derivative thereof and at least one pharmaceutically acceptable diluent, excipient, or carrier, for use in treating or preventing a condition of a nasal or a paranasal mucous membrane in a human subject in need thereof, wherein the condition is selected from the group consisting of nasal congestion and nasal hemorrhages ("nose bleeds").

Embodiment 31 is a method of treating or preventing a condition of a nasal or paranasal mucous membrane in a subject in need thereof, the method comprising administering to the nasal or paranasal mucous membrane of the subject the pharmaceutical composition of embodiments 25-27.

Embodiment 32 is a method of preparing an aqueous pharmaceutical composition, comprising combining about 0.1 mg/ml to 2.0 mg/ml of (S)-(1-methyl-2-pyrrolidinyl)-pyridine or a pharmaceutically acceptable salt, analog, precursor, or derivative thereof and at least one pharmaceutically acceptable diluent, excipient, or carrier to obtain the aqueous pharmaceutical composition.

Embodiment 33 is the method according to any one of embodiments 1-24, wherein the pharmaceutically acceptable diluent, excipient or carrier comprises a preservative, preferably salicylic acid.

Embodiment 34 is the method of embodiment 35, wherein the preservative is salicylic acid at a concentration of about 0.5 mg/ml.

Embodiment 35 is the pharmaceutical composition according to any one of embodiments 25-27, wherein the pharmaceutically acceptable diluent, excipient or carrier comprises a preservative, preferably salicylic acid.

Embodiment 36 is the pharmaceutical composition according to embodiment 35, wherein the preservative is salicylic acid at a concentration of about 0.5 mg/ml.

I claim:

1. A method of treating a condition of a nasal or paranasal mucous membrane in a subject in need thereof, the method comprising administering to the nasal or paranasal mucous membrane of the subject a therapeutically effective amount of a pharmaceutical composition comprising a nicotinic acetylcholine receptor (nAChR) agonist selected from the group consisting of (S)-(1-methyl-2-pyrrolidinyl)-pyridine, (R)-(1-methyl-2-pyrrolidinyl)-pyridine, or a mixture thereof, or a pharmaceutically acceptable salt, analog, or precursor thereof and at least one pharmaceutically acceptable diluent, excipient, or carrier, wherein the condition of the nasal or paranasal mucous membrane is selected from the group consisting of rhinitis; allergic rhinitis; acute rhinitis; atrophic rhinitis; vasomotor rhinitis; chronic or recurrent sinusitis; an inflammation; a chronic inflammatory disease; an acute inflammatory disease; hemorrhages; minor bleeding; a chronic degenerative disease; an acute degenerative disease; edema of the mucous membranes; edema of one or more turbinates; postnasal drainage; facial pressure and pain; headaches; dripping of mucous membrane secretions down the throat; post nasal drip; abnormal taste sensations; feeling of dryness in the upper respiratory tract; drowsiness; nasal irritation; a loss of the sense of smell; burning sensations within the nose; ear or hearing issues; itchy nose; itchy eyes; sneezing; snoring; sleep apnea; asthma; nasal polyps (nasal polyposis); and exposure to environmental irritants or allergens.

2. The method of claim 1, wherein the nAChR agonist is (S)-(1-methyl-2-pyrrolidinyl)-pyridine or a pharmaceutically acceptable salt thereof.

3. The method of claim 1, wherein the subject is a human subject.

4. The method of claim 1, wherein the condition of the nasal or paranasal mucous membrane is selected from the group consisting of rhinitis, allergic rhinitis, acute rhinitis, atrophic rhinitis, vasomotor rhinitis, chronic or recurrent sinusitis, an inflammation, a chronic inflammatory disease, an acute inflammatory disease, hemorrhages, minor bleeding, a chronic degenerative disease, an acute degenerative disease, edema of the mucous membranes, and edema of one or more turbinates.

5. The method of claim 1, wherein the condition of the nasal or paranasal mucous membrane is at least one selected from the group consisting of postnasal drainage; facial pressure and pain; headaches; dripping of mucous membrane secretions down the throat; post nasal drip; abnormal taste sensations; feeling of dryness in the upper respiratory tract; drowsiness; nasal irritation; a loss of the sense of smell; burning sensations within the nose; ear or hearing issues; itchy nose; itchy eyes; sneezing; snoring; sleep apnea; asthma; nasal polyps (nasal polyposis); and exposure to environmental irritants or allergens.

6. The method of claim 1, wherein a concentration of the nAChR agonist is about 0.1 mg/ml to 2.0 mg/ml.

7. The method of claim 1, wherein a concentration of the nAChR agonist is about 0.1 mg/ml to 0.5 mg/ml.

8. The method of claim 1, wherein the pharmaceutical composition is an aqueous solution.

9. The method of claim 1, wherein the pharmaceutically acceptable diluent, excipient, or carrier comprises methylcellulose at a concentration of about 0.5% by weight to 1% by weight based on a total weight of the composition.

10. The method of claim 1, wherein the pharmaceutical composition is administered nasally.

11. The method of claim 1, wherein the pharmaceutical composition is administered by drops, a nasal aerosol spray, an ointment or a gel.

12. The method of claim 1, wherein the pharmaceutical composition is administered in a dose of one or two drops per nostril with each drop having a volume of about 0.01 ml to 0.1 ml, and the administration is optionally repeated two to four times daily.

13. The method of claim 1, wherein the pharmaceutical composition is administered nasally by topical application to:
   a. one or more mucous membranes of the nasal cavity of a superior turbinate, a middle turbinate and an inferior turbinate olfactory bulb; and/or
   b. one or more mucous membranes of the paranasal sinuses of a frontal sinus, a sphenoid's sinus, a maxillary sinus and an ethmoid sinus.

14. The method of claim 1, further comprising treating the subject with a phototherapy.

15. A method of treating nasal hemorrhages ("nose bleeds") in a human subject in need thereof, the method comprising nasally administering to the nasal or paranasal mucous membrane of the subject a therapeutically effective amount of an aqueous pharmaceutical composition comprising about 0.1 mg/ml to 2.0 mg/ml of (S)-(1-methyl-2-pyrrolidinyl)-pyridine or a pharmaceutically acceptable salt thereof and at least one pharmaceutically acceptable diluent, excipient, or carrier, wherein the condition is.

16. The method of claim 15, wherein the pharmaceutically acceptable carrier, diluent or excipient comprises methylcellulose at a concentration of 0.5% by weight to 1% by weight based on a total weight of the composition.

17. The method of claim 15, wherein the pharmaceutical composition is administered by drops or a nasal aerosol spray.

18. The method of claim 15, wherein the aqueous pharmaceutical composition is administered in a dose of one or two drops per nostril with each drop having a volume of about 0.01 ml to 0.1 ml, and the administration is optionally repeated two to four times daily.

19. The method of claim 15, further comprising treating the human subject with a phototherapy.

20. A pharmaceutical composition comprising:
   a. (S)-(1-methyl-2-pyrrolidinyl)-pyridine or a pharmaceutically acceptable salt thereof at a concentration of about 0.1 mg/ml to 2 mg/ml; and
   b. a diluent, an excipient or a carrier suitable for a nasal administration comprising methylcellulose at a concentration of 0.5% by weight to 1% by weight based on a total weight of the composition; and salicylic acid at a concentration of about 0.5 mg/ml.

* * * * *